US00PP12822P2

(12) United States Plant Patent
Moolenaar

(10) Patent No.: US PP12,822 P2
(45) Date of Patent: Aug. 6, 2002

(54) PLUMBAGO PLANT NAMED 'BCT9805PLU'

(75) Inventor: Alfred Nicol Moolenaar, Voorhout (NL)

(73) Assignee: BCT Bio Chemical Technologies AG, Zug (CH)

( * ) Notice: Subject to any disclaimer, the term of this patent is extended or adjusted under 35 U.S.C. 154(b) by 53 days.

(21) Appl. No.: 09/797,253

(22) Filed: Mar. 1, 2001

(51) Int. Cl.[7] ..... A01H 5/00
(52) U.S. Cl. ..... Plt./226
(58) Field of Search ..... Plt./226

(56) References Cited

PUBLICATIONS

GTITM UPOVROM Citation for 'BCT9805PLU' as per NL PBR LDK0001; Mar. 13, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Plumbago plant named 'BCT9805PLU', characterized by its compact plant habit; densely foliated habit; freely flowering habit; and dark pink flower color.

1 Drawing Sheet

BACKGROUND OF THE INVENTION

The present Invention relates to a new and distinct cultivar of Plumbago plant, botanically known as *Plumbago indica*, and hereinafter referred to by the name 'BCT9805PLU'.

The new Plumbago originated from a cross made by the Inventor of two unidentified selections of *Plumbago indica*. The cultivar 'BCT9805PLU' was discovered and selected by the Inventor as a single plant within the progeny of the stated cross in a controlled environment in Voorhout, The Netherlands in 1997. The selection of this plant was based on its compact plant habit and numerous leaves.

Asexual reproduction of the new cultivar by tissue culture since 1998 in Voorhout, The Netherlands, has shown that the unique features of the new Plumbago are stable and reproduced true to type in successive generations.

SUMMARY OF THE INVENTION

Plants of the cultivar 'BCT9805PLU' have not been observed under all possible environmental conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'BCT9805PLU'. These characteristics in combination distinguish 'BCT9805PLU' as a new and distinct cultivar:

1. Compact plant habit.
2. Densely foliated.
3. Freely flowering habit.
4. Dark pink flower color.

Plants of the cultivar 'BCT9805PLU' can be compared to plants of the parent selections, the unidentified selection of *Plumbago indica*. In side-by-side comparisons conducted by the Inventor in Voorhout, The Netherlands, plants of the new Plumbago differed from plants of the unidentified Plumbago selections in the following characteristics:

1. Plants of the new Plumbago are more compact and more densely foliated than plants of the unidentified Plumbago selections.
2. Plants of the new Plumbago have thicker and stronger leaves than plants of the unidentified Plumbago selections.
3. Plants of the new Plumbago are more freely flowering than plants of the unidentified Plumbago selections.

BRIEF DESCRIPTION OF THE PHOTOGRAPH

The accompanying colored photograph illustrates the overall appearance of the new Plumbago, showing the colors as true as it is reasonably possible to obtain in colored reproductions of this type. Colors in the photograph may differ slightly from the color values cited in the detailed botanical description which accurately describe the colors of the new Plumbago. The photograph comprises a side perspective view of a typical flowering plant of 'BCT9805PLU' grown in a container that was pinched twice and was about 8 months from planting.

DETAILED BOTANICAL DESCRIPTION

In the following description, color references are made to The Royal Horticultural Society Colour Chart except where general terms of ordinary dictionary significance are used. Plants used for the following description were pinched, were about 8 months old and grown in 17-cm containers in a glass-covered greenhouse and with cultural conditions which closely approximate commercial production conditions in Voorhout, The Netherlands. During the production, day and night temperatures ranged from 16 to 21° C.

Botanical classification: *Plumbago indica* cultivar 'BCT9805PLU'.

Parentage: Seedling from cross-pollination of two unidentified selections of *Plumbago indica,* not patented.

Propagation:

*Type cutting*.—By tissue culture.

*Time to initiate roots*.—About three weeks at 21° C.

*Time to develop roots*.—About four weeks at 18° C.

*Root description*.—Freely branching, fine.

Plant description:

*Form*.—Upright flowering plant with basal leaves; salverform flowers arranged on erect spikes. Appropriate for 17-cm containers. Moderately vigorous.

*Plant height*.—About 40 cm.

*Plant diameter*.—About 25 cm.

*Lateral branch/peduncle description*.—Quantity per plant: Typically five after pinching. Length: About 30 cm. Diameter: About 4 mm. Internode length: About 8 cm. Texture: Glabrous; slightly ribbed. Color: 147A.

*Foliage description*.—Leaves simple, generally symmetrical, alternate and long-persisting. Quantity per lateral branch: About 8. Length: About 15 cm. Width: About 7 cm. Shape: Ovate to elliptic. Apex: Acute to rounded. Base: Obtuse to cuneate. Margin: Entire. Texture: Glabrous; somewhat rugose. Color: Young foliage, upper and lower surfaces: 137A. Mature foliage, upper and lower surfaces: 147A; veins, 147A. Petiole: Length: About 1 cm. Diameter: About 3 mm. Color: 147A.

Flower description:

*Appearance*.—Single salverform flowers arranged on upright spikes. Flowers not persistent.

*Quantity of flowers*.—Freely flowering; one flowering spike per lateral branch, about 100 flowers per spike will develop during the flowering season.

*Natural flowering season*.—In the summer in The Netherlands; flowering continuous.

*Fragrance*.—Not fragrant.

*Flower longevity on the plant*.—About 1 or 2 days.

*Flower size*.—Diameter: About 3 cm. Depth: About 2.5 cm.

*Flower buds* (*at stage of showing color*).—Length: About 2 to 2.5 cm. Diameter: About 2 mm. Shape: Tubular. Color: 52A.

*Petals*.—Quantity per flower: Five per flower, fused at base. Length: About 1.5 cm. Width: about 1 cm. Shape, above throat: Roughly elliptic. Apex: Rounded to acute. Margin: Entire. Texture: Smooth, glabrous. Color: When opening and fully opened, upper surface: 52B. When opening and fully opened, lower surface: 52C to 52D.

*Sepals*.—Quantity per flower: Five per flower, fused at base. Calyx length: About 1 cm. Calyx diameter: About 2 mm. Shape: Linear. Apex: Acute. Margin: Entire. Texture: Glandular reddish pubescence. Color: Upper surface: 137A with reddish anthocyanin towards apex. Lower surface: 137A.

*Pedicel*.—Length: About 1 mm. Angle: About 30° from vertical. Strength: Strong. Color: 147A.

*Reproductive organs*.—Stamens: Quantity: About 5 per flower. Anther size: About 3 by 1 mm. Anther color: Pinkish. Pollen amount: Scarce. Pistils: Quantity: 1 per flower. Pistil length: About 2.8 cm. Style length: About 2.5 cm. Style color: Light pink. Stigma color: Light pink.

*Seed*.—Seed production has not been observed.

Disease resistance: Plants of the new Plumbago have not been noted to be resistant to pathogens common to Plumbago.

Weather tolerance: Plants of the new Plumbago have been observed to be tolerant to temperatures ranging from 10 to 35° C. and have been observed to be tolerant to wind and rain.

It is claimed:

1. A new and distinct cultivar of Plumbago plant named 'BCT9805PLU', as illustrated and described.

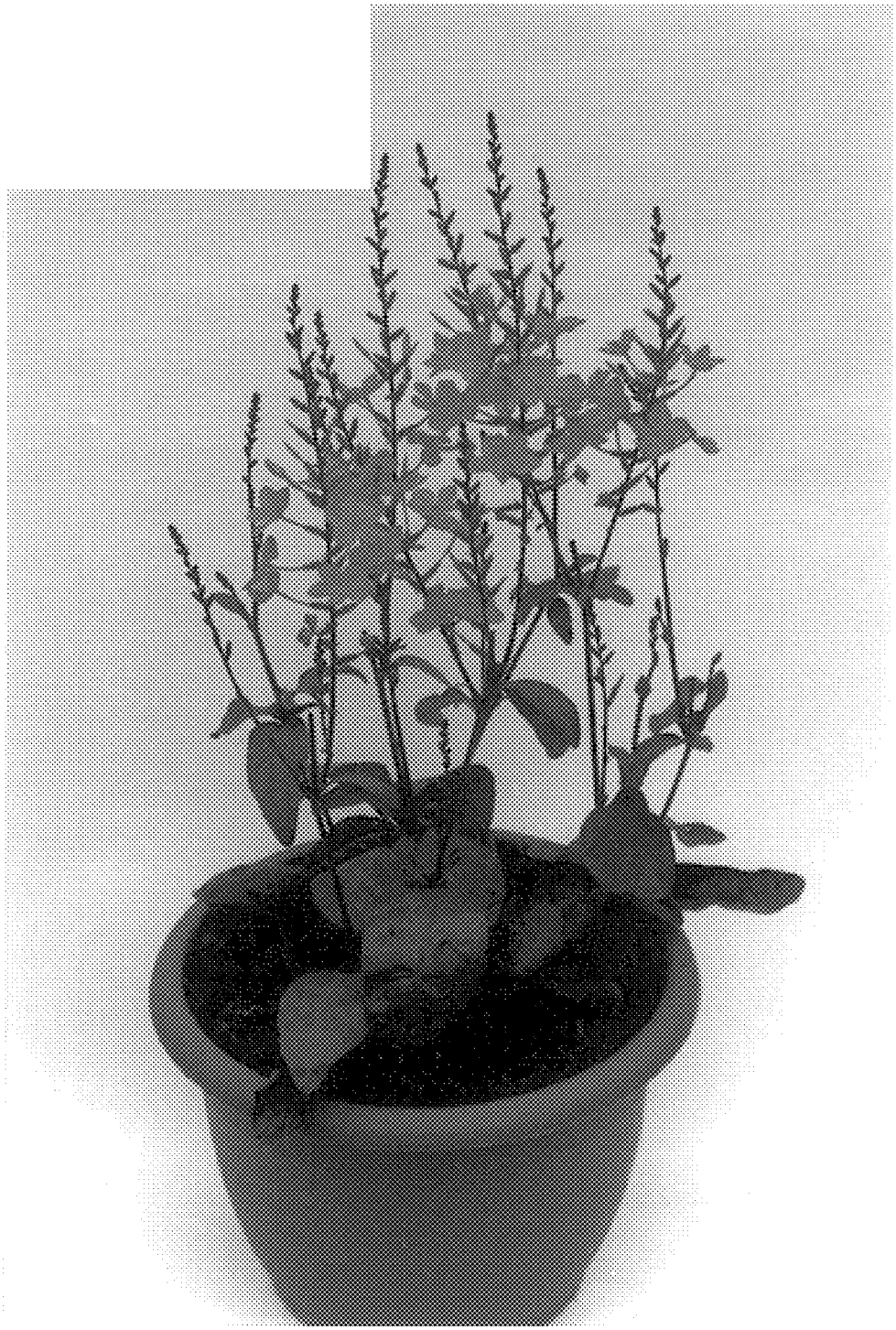

* * * * *